United States Patent [19]

Ossip et al.

[11] 4,087,456
[45] May 2, 1978

[54] PURIFICATION OF OLEOPHILIC HYDROCARBON SULFONATE PRODUCT MIXTURES

[75] Inventors: Paul S. Ossip, Denver; Larry M. Echelberger, Littleton, both of Colo.

[73] Assignee: Marathon Oil Company, Findlay, Ohio

[21] Appl. No.: 301,572

[22] Filed: Oct. 27, 1972

[51] Int. Cl.$^2$ ............................................. C07C 143/24
[52] U.S. Cl. .............................. 260/505 P; 252/8.5 C; 252/8.55 D
[58] Field of Search ...................................... 260/505 P

[56] References Cited

U.S. PATENT DOCUMENTS

| | | | |
|---|---|---|---|
| 1,868,596 | 7/1932 | Eichwald | 260/505 |
| 2,223,194 | 11/1940 | Thompson | 260/505 |
| 2,280,118 | 4/1942 | Dombrow | 260/505 |

*Primary Examiner*—A. Siegel
*Attorney, Agent, or Firm*—Joseph C. Herring; Jack L. Hummel

[57] ABSTRACT

Addition of small amounts of water and small amounts of neutral oleophilic organic compounds, e.g., alcohols, phenols, aldehydes, ketones, and esters to product mixtures produced by treatment of hydrocarbons with sulfur trioxide, followed by neutralization with an inorganic hydroxide, and comprising oleophilic petroleum sulfonates, together with undesired hydrophilic petroleum sulfonates and inorganic salts, causes separation of a lower phase containing substantial quantities of said undesired constituents and permitting ready recovery of said oleophilic hydrocarbon sulfonates. The products are particularly useful in micellar systems for the secondary-type recovery of petroleum.

5 Claims, No Drawings

PURIFICATION OF OLEOPHILIC HYDROCARBON SULFONATE PRODUCT MIXTURES

CROSS REFERENCES TO RELATED APPLICATIONS

The applicants know of no United States Patent applications closely related to the invention.

BACKGROUND OF THE INVENTION

1. Field of the Invention

The present invention relates to the field of compositions for oil treating, generally classified in United States Patent Office Class 252, subclass 8.55 and to Chemistry of the Carbon Compounds, Sulfonation Products of aromatic mixtures, generally classified in Class 260, subclass 5.05.

2. Description of the Prior Art

A wide variety of prior art patents have taught the production of petroleum sulfonates, e.g., U.S. Pat. Nos. 3,183,183; 2,990,812; 3,215,628; 2,197,800; 2,815,370; 2,845,455; 2,174,508; 2,800,962; 3,173,864; 3,308,068; 3,244,622 and 3,418,239.

In the above references and in many other patented and non-patented literature references, hydrocarbon sulfonates are prepared by contacting hydrocarbons with sulfur trioxide or with sulfuric acid. However, to the best of our knowledge, none of these references has achieved the simplicity and attendant economy in the purification of the product mixtures resulting from such sulfonations which are achieved by the present invention.

SUMMARY OF THE INVENTION

General Statement of the Invention

According to the present invention, sulfur trioxide is contacted with a hydrocarbon, then neutralized with an inorganic hydroxide to form a product mixture comprising oleophilic sulfonates, together with undesirable hydrophilic sulfonates and inorganic acid salts, e.g., sulfites and sulfates. The desired oleophilic sulfonates are separated from a substantial portion of these undesirable impurities by the simple addition of water plus a neutral oleophilic organic compound, e.g., alcohols, phenols, aldehydes, ketones, and esters, to such product mixtures produced by the treatment of hydrocarbons with sulfur trioxide. Optionally, the neutralized product mixture is contacted initially with water in order to effect separation of an upper phase containing mainly unreacted hydrocarbon. This upper phase is removed and then the neutral oleophilic organic compound is added to the lower (product) phase to effect separation of the brine phase.

The invention thus provides a simple and unusually economic method for the production of oleophilic petroleum sulfonates of sufficient purity for many commercial applications.

Utility of the Invention

Petroleum sulfonates are useful in a wide variety of detergent applications and in the preparation of micellar systems which are in turn utilized for such purposes as the displacement of petroleum from subterranean formations. The low cost sulfonates of the present invention are especially useful in secondary-type recovery of petroleum by sulfonate floods, emulsion floods, micellar system floods, and other processes of flooding the formations with displacement media which comprise sulfonates.

DESCRIPTION OF THE PREFERRED EMBODIMENTS

Starting Materials

Oleophilic Organic Compounds: The oleophilic organic compounds do not enter into deleterious side reactions. Preferred oleophilic organic compounds include $C_5+$ alcohols, e.g., pentanols hexanols, octanols, and hydrocinnamyl alcohol, $C_7+$ phenols, e.g., p-nonylphenol, butylphenols, and cresols, $C_7+$ aldehydes, e.g., heptaldehyde, caprylaldehyde, and ethylhexanol, and $C_6+$ ketones, cyclohexanone, dibutyl ketone, and dipentyl ketone, $C_8+$ esters, e.g., butyl butyrate, ethyl octanoate, and octyl acetate, and also mixtures of the foregoing. Especially preferred neutral oleophilic organic compounds include hexanols, octanols, p-nonylphenol, heptaldehyde, cyclohexanone, and mixtures of the foregoing. The neutral oleophilic compound will contain preferably from the minimum number of carbon atoms specified above to about $C_{20}$. The most preferred oleophilic organic compound is hexanol.

Normally from about 0.05 to about 10.0, more preferably from about 0.10 to about 5.0, and most preferably from about 0.25 to about 2.0 moles of neutral oleophilic organic compound per mole of sulfonate groups in the product mixture will be added to the product mixture.

Water: The water utilized with the present invention will preferably be fresh water but can be brackish, e.g., Palestine water.

From about 5 to about 500, more preferably from about 10 to about 250, and most preferably from about 25 to about 100 moles of water will be added per mole of organic sulfonate groups in said product mixture.

Temperature: The temperature for the conducting of the process of the present invention will generally be in the range of from about 0° to about 100° C., more preferably from about 15° to about 75° C., and most preferably from about 30° to about 60° C.

Pressure: While the process of the present invention could be conducted under super atmospheric or subatmospheric pressure, it will normally be conducted at prevailing atmospheric pressure. Neither pressure nor temperature are narrowly critical for the conducting of the process.

Time: While not narrowly critical, the time for the formation of the phases will generally be in the range of from about ½ hr. to about 48 hrs., more preferably from about 1 hour to about 24 hrs., and most preferably from about 2 hrs. to about 12 hours.

Batch or Continuous Basis: While the examples describe the conventional or batch basis, it may, of course, be practiced on a continuous basis with continuous flows of the additives and the sulfonate product mixture into a mixing tank and with continuous separation of the phases by centrifugation, continuous decantation or other conventional techniques.

Apparatus: The apparatus of the invention is not critical and may be the reactor in which the sulfonate product mixture was produced or may, as mentioned directly above, include continuous apparatus with flows in and out. The conventional apparatus and materials for construction can be readily selected by those skilled in the art.

EXAMPLES

EXAMPLE I 400 grams of Northern Crawford County crude oil is sulfonated with 9.6 weight percent of $SO_3$ in the presence of ethylene dichloride solvent. The reaction mixture is neutralized with ammonium hydroxide and stripped by flash evaporation at 120° F., and 50 mm Hg to remove the reaction solvent to give 350 grams of unextracted sulfonate. 200 grams of water is added to the product mixture in a separatory funnel, and an upper raffinate phase weighing 117 grams forms within about 8 hrs. and is separated by withdrawing the lower product phase. Hexanol (17.5 ml) is then added to the product phase in a separatory funnel, and a lower brine phase weighing 32.5 grams and containing 2.9 percent of $-SO_3NH_4$ groups and 9.70 percent of salt (by weight) forms in about 60 minutes and is removed by gravity flow. This phase contains approximately 4% of the total sulfonate groups produced. The sulfonate product has the following composition: 6.5 weight percent $-SO_3NH_4$ groups; 3.9% $(NH_4)_2SO_4$; 30.3% $H_2O$; 3.64% Hexanol.

EXAMPLE II

The sulfonate produced in Example I (53.85 grams) is mixed with 1.5% aqueous ammonia solution (45.68 grams), filtered Henry crude Oil (2.47 grams), isopropanol (4.73 grams), to provide a micellar system which is used to displace residual oil from a 3 inches diameter × 4 feet long fired Berea core (having 273 millidarcy permeability and 19.6% porosity) previously saturated with Henry (Illinois field) crude oil, then water flooded with 0.61 pore volumes of synthetic Henry Plant water (containing 18,000 ppm NaCl, 518 ppm $CaCl_2$, 267 ppm $MgCl_2$). The residual oil saturation is 32% after waterflooding. The core is then flooded with 0.04 pore volumes of the above micellar system driving by 0.1 pore volumes of Palestine water thickened with 1000 ppm. Nalco NX 586-71 polymer, followed by 0.6 pore volumes of Palestine water thickened with 529 ppm of that Nalco polymer, followed by 0.53 pore volumes unthickened Palestine water. The flooding is done over a period of 25 hours at about 75° F. Substantially all of the residual oil is recovered from the core by this tertiary flooding.

EXAMPLE III (Comparative, using conventional unextracted sulfonate)

A micellar system (28.74 grams of sulfonate having a composition of 12.18% by weight $-SO_3NH_4$ groups; 6.80% by weight $(NH_4)SO_4$; 7.95% $H_2O$ and zero percent alcohol; 67.72 grams of 1.5% aqueous ammonia solution; 3.55 grams of Henry crude oil) is used to flood a Berea core. The preparation of the core and the techniques of flooding are substantially identical with those described in Example II, above. The oil recovery is substantially less than that of Example II.

Modifications of the Invention

It should be understood that the invention is capable of a variety of modifications and variations which will be made apparent to those skilled in the art by a reading of the specification and which are to be included within the spirit of the claims appended hereto.

What is claimed is:

1. In a process for the production of hydrocarbon sulfonates by reaction of sulfur trioxide with aromatic hydrocarbons at temperatures in the range of from about 0 to about 100° C., followed by neutralization with an inorganic hydroxide, to form a product mixture comprising oleophilic hydrocarbon sulfonates, undesired hydrophilic hydrocarbon sulfonates, and undesired inorganic sulfites and inorganic sulfates, the improvement comprising in combination the steps of:
    (a) adding to said product mixture after neutralization from about 0.05 to about 10.0 moles of a neutral oleophilic organic compound and from 5 to about 500 moles of water, both per mole of sulfonate groups in said product mixtures,
    (b) allowing separation to provide a lower phase containing substantial amounts of said undesired inorganic sulfates, inorganic sulfites, and hydrophilic hydrocarbon sulfonates and water, and an upper phase comprising substantial amounts of said desired oleophilic hydrocarbon sulfonates, together with substantial amounts of neutral oleophilic organic compound, and thereafter, recovering at least a portion of said upper phase.

2. A process according to claim 1 wherein said neutral oleophilic organic compound is selected from the group consisting of neutral oleophilic alcohols, phenols, aldehydes, ketones, and esters, and mixtures of the foregoing.

3. A process according to claim 1 wherein said water is added to said product mixture prior to the addition of said neutral oleophilic organic compound, and wherein after the addition of said water phase, separation is permitted to form an upper and a lower phase, said upper phase comprising unreacted hydrocarbon, and wherein said upper phase is substantially removed from said lower phase and said neutral oleophilic organic compound is thereafter added to said lower phase to form said upper and lower phases as described in claim 1.

4. A process according to claim 1 wherein said neutral oleophilic organic compound comprises a hexanol.

5. A process according to claim 1 wherein said neutral oleophilic organic compound comprises n-hexanol.

* * * * *